(12) United States Patent
Bobst et al.

(10) Patent No.: US 7,125,665 B2
(45) Date of Patent: Oct. 24, 2006

(54) DETECTION OF NUCLEIC ACID TARGET SEQUENCES BY ELECTRON PARAMAGNETIC RESONANCE SPECTROSCOPY

(75) Inventors: Albert M. Bobst, 1271 Grace Ave., Cincinnati, OH (US) 45208; Jeffery D. Hester, Cincinnati, OH (US)

(73) Assignee: Albert M. Bobst, Cincinnati, OH (US)

( * ) Notice: Subject to any disclaimer, the term of this patent is extended or adjusted under 35 U.S.C. 154(b) by 401 days.

(21) Appl. No.: 10/182,559

(22) PCT Filed: Jan. 26, 2001

(86) PCT No.: PCT/US01/02672

§ 371 (c)(1),
(2), (4) Date: Nov. 25, 2002

(87) PCT Pub. No.: WO01/55438

PCT Pub. Date: Aug. 2, 2001

(65) Prior Publication Data

US 2003/0211492 A1    Nov. 13, 2003

Related U.S. Application Data

(60) Provisional application No. 60/178,096, filed on Jan. 26, 2000.

(51) Int. Cl.
*C12Q 1/68* (2006.01)
(52) U.S. Cl. .......................................................... 435/6
(58) Field of Classification Search .................. 536/29, 536/25.32; 435/6, 91.2, 91
See application file for complete search history.

(56) References Cited

U.S. PATENT DOCUMENTS 5,004,809 A * 4/1991 Bobst et al. ............... 536/24.3
5,210,015 A   5/1993 Gelfand et al.
5,573,907 A   11/1996 Carrino et al.
5,716,784 A * 2/1998 Di Cesare .................... 435/6
5,925,517 A   7/1999 Tyagi et al.

OTHER PUBLICATIONS

Spielmann, et al., "Spin-labeled Psoralen Probes for the Study of DNA Dynamics," Biochemistry 1995, vol. 34, pp. 14801-14814.
Strobel, et al., "Preparation and Characterization of Spin-Labeled Oligonucleotides for DNA Hybridization," Bioconjugate Chemistry, 1991, pp. 89-95.
Hester, et al., "Identification of a Single Genome by Electron Paramagnetic Resonance (EPR) with Nitroxide-Labeled Oligonucleotide Probes," University of Cincinnati, Oct. 26, 2001.

* cited by examiner

*Primary Examiner*—Jeffrey Fredman
*Assistant Examiner*—Heather G. Calamita
(74) *Attorney, Agent, or Firm*—Frost Brown Todd LLC

(57) ABSTRACT

The present invention relates to methods and kits for detecting the presence or absence of a target DNA sequence, such as a mutation, within an identified region of a selected DNA molecule, such as a gene. In particular aspects, the invention relates to the use of certain aspects of the polymerase chain reaction ("PCR") and ligase chain reaction ("LCR") techniques for the detection of genetic mutations in genes, particularly point mutations. A kit has been developed for direct EPR detection of specific PCR amplified target nucleic acid sequences. The PCR reaction is carried out in the presence of nitroxide-labeled oligomers that are degraded only if hybridized to a complementary target sequence. The degradation of the nitroxide-labeled oligomers into nitroxide-labeled cleavage products results in a characteristic increase of the h-/ho ratio of the EPR signal; in the absence of a complementary target sequence the EPR signal of nitroxide-labeled oligomer remains unchanged.

9 Claims, 5 Drawing Sheets

0.17nmol spin-labeled 19-mer hybridization probe
(nitroxide away from 5'-end 0.32nmol spin-labeled 25-mer hybridization probe
(nitroxide at 5' end)

DETECTION OF NUCLEIC ACID TARGET SEQUENCES BY ELECTRON PARAMAGNETIC RESONANCE SPECTROSCOPY

CROSS-REFERENCE TO RELATED APPLICATIONS

This application claims the benefit of International Patent Application No. PCT/US01/02672, filed Jan. 26, 2001, which claims the benefit of U.S. Provisional Patent Application Ser. No. 60/178,096 filed Jan. 26, 2000, of which both applications are hereby incorporated by reference in their entirety.

FIELD OF THE INVENTION

The present invention relates to methods and kits for detecting the presence or absence of a target DNA sequence, such as a mutation, within an identified region of a selected DNA molecule, such as a gene. In particular aspects, the invention relates to the use of certain aspects of the polymerase chain reaction ("PCR") and ligase chain reaction ("LCR") techniques for the detection of genetic mutations in genes, particularly point mutations. A kit has been developed for direct EPR detection of specific PCR amplified target nucleic acid sequences. The PCR reaction is carried out in the presence of nitroxide-labeled oligomers that are degraded only if hybridized to a complementary target sequence. The degradation of the nitroxide-labeled oligomers into nitroxide-labeled cleavage products results in a characteristic increase of the h-/ho ratio of the EPR signal; in the absence of a complementary target sequence the EPR signal of nitroxide-labeled oligomer remains unchanged.

DESCRIPTION OF THE RELATED ART

The ability to detect specific nucleotide DNA sequences such as genes is an invaluable tool for medical science. The ability to identify alterations provides a means for diagnosis of genetic diseases that involve DNA mutations, including sickle- cell anemia, thalassemia, diabetes, certain oncogenic mutations, and the like. Importantly, the ability to diagnose genetic diseases such as the foregoing would provide numerous advantages, ranging from the ability to prepare for proper care and treatment of affected individuals, such as in the case of prenatal diagnosis, to marital counseling of prospective parents. Unfortunately, the techniques presently available to medical science for such diagnosis have been generally quite limited in one or more aspects.

Single base variations have been analyzed by a variety of techniques, such as restriction fragment length polymorphism, denaturing gradient gel electrophoresis and chemical cleavage of mismatched heteroduplexes. Other techniques include RNase cleavage of mismatched bases and single strand conformation polymorphism. All of these techniques have the advantage of being able to screen for unknown mutations. Yet, they are very labor intensive, multi-step, non-auto mated processes and most importantly lack sensitivity.

This invention relates to probes for use in DNA or RNA polynucleotide hybridization assays to provide improved detection characteristics and more particularly to an assay system with improved sensitivity for detection of polynucleotide sequences using electronic spin resonance (ESR) probes in PCR hybridization assays, particularly homogeneous PCR hybridization assays.

Polymerase chain reaction (PCR) is a recently developed significant and powerful technique for polynucleotide amplification. The technique is disclosed, for example, in U.S. Pat. Nos. 4,683,195; 4,683,202; 4,800,159 and 4,965, 188. PCR may be generally described as follows. The technique is an enzymatic, in vitro synthesis method for replicating or amplifying specific target polynucleotide sequences in samples. The technique employs polymerase, deoxynucleoside triphosphates and two oligonucleotide primers that hybridize to opposite strands of the polynucleotide sample and flank the region of interest in the target polynucleotide sequence. Experimental amplification of the target sequence is obtained by a repetitive series of steps comprising template denaturation, primer annealing and extension of the annealed primers by polymerase, generally referred to as thermal cycling steps. Such a PCR technique is capable of producing amplification of the target sequence by a factor of up to about $10^{12}$.

Once a polynucleotide sample is subject to amplification in an amplification procedure, detection of the presence or absence of the desired target sequence can be accomplished by a variety of radiative (isotopic) or non-radiative (non-isotopic) hybridization detection methods. Such hybridization assays are disclosed, for example, in Methods of Enzymology, Vol. 68, pp 379–469 (1979) and Vol. 65, Part 1, pp 468–478 (1978) and in Analytical Biochemistry, 138, pp 267–284 (1984) and describe the use of radiative (isotopic) labeled and fluorescent labeled detection probes. In recent time, much effort has been made to move away from radioactively labeled probes and towards the use of fluorescent-labeled probes.

Currently, assay formats are predominantly based on heterogeneous hybridization in which the target nucleic acid is sequestered on a solid support to permit separation of hybridized and unhybridized detection probes. Fluorescence detection assays for hybridization systems are well known in the art as described in U.S. Pat. Nos. 5,925,517, 5,716,784, incorporated herein by reference. While these heterogeneous assays display good sensitivity, the necessity for separation and wash steps makes automation difficult.

While simpler to carry out homogeneous assay procedures based on chemi- or bio- luminescent probes have been reported, unbound labeled probe remains in solution causing undesirable interfering background signal. It is therefore desirable to provide an improved assay procedure for enhanced detection of target polynucleotide samples using ESR permitting both amplification of the target and release of a label for detection to be accomplished in a reaction system without requiring a multitude of handling or separation steps of the amplified product and especially useful for homogeneous assays in which an assay signal can be generated while the target sequence is amplified and without requiring separation steps.

Other relevant references include U.S. Pat. Nos. 5,925, 517, 5,716,784, and 5,210,015.

BRIEF SUMMARY OF THE INVENTION

The present invention relates to methods and kits for detecting the presence or absence of a target DNA sequence, such as a mutation, within an identified region of a selected DNA molecule, such as a gene. In particular aspects, the invention relates to the use of certain aspects of the polymerase chain reaction ("PCR") and ligase chain reaction ("LCR") techniques for the detection of genetic mutations in genes, particularly point mutations. A kit has been developed for direct EPR detection of specific PCR amplified target nucleic acid sequences. The PCR reaction is carried out in the presence of nitroxide-labeled oligomers that are degraded only if hybridized to a complementary target sequence. The degradation of the nitroxide-labeled oligomers into nitroxide-labeled cleavage products results in a characteristic increase of the h-/ho ratio of the EPR signal; in the absence of a complementary target sequence the EPR signal of nitroxide-labeled oligomer remains unchanged.

In one embodiment, the present invention provides a method for detecting the presence or absence of a target nucleic acid sequence in a sample, said process comprising:
  a) providing in a PCR reaction mixture a sample suspected to contain a target nucleic acid sequence, oligonucleotide PCR primers that hybridize to the target nucleic acid sequence for PCR amplification of said target sequence, each of four deoxynucleoside triphosphates, nucleic acid polymerase having 5' to 3' exonuclease activity and devoid of 3' to 5' exonuclease activity, and an EPR-labeled oligonucleotide analytical probe (EPR probe)
  b) amplifying target nucleic acid sequence in the sample under suitable PCR reaction mixture temperature conditions by a repetitive series of PCR thermal cycling steps comprising:
    1) denaturing the target nucleic acid sequence into opposite strands;
    2) hybridizing the EPR probe within the target nucleic acid sequence of the denatured strands and hybridizing the oligonucleotide PCR primers to the denatured strands, and
    3) extending the hybridized primers with the four deoxynucleoside triphosphates and the nucleic acid polymerase, and producing preferentially 5' EPR labeled nucleotide fragments during this extension phase by the 5' to 3' exonuclease activity of the nucleic acid polymerase on EPR probe annealed to the denatured strands;
  c) following amplification of the target nucleic acid sequence by one or more series of thermal cycling steps, detecting or measuring the magnetic resonance as a measure of the presence of the target nucleic acid sequence.

In contrast to approaches based on fluorescence spectroscopy developed by others the proposed magnetic resonance detection (EPR) with nitroxide labeled oligomers offers the advantage of no interference by turbidity of the solution, no interference by the hydrophobic properties of the fluorochromes, no tedious and expensive labeled oligomer synthesis, but most importantly, no interference by potential fluorescent background signals. While the fluorescent based technology relies on some complex mechanism responsible for the increase of fluorescence in the presence of two labels (one with fluorescent and one with quenching properties) in the PCR mixture, the nitroxide-labeled oligomer based assay relies on a theoretically more readily understood EPR line-shape change (h-/ho ratio change) due to one label only, namely the nitroxide label, whereas fluorescent based assays usually require two labels.

Nitroxide labeled nucleotides and nitroxide labeled hybridization probes are known in the art as described in U.S. Pat. No. 5,004,809, incorporated herein by reference. Besides using the already known nitroxide labeled hybridization probes, it is foreseen many other nitroxide labeled oligonucleotides may be prepared using known methods.

The nitroxide label methods of the present invention can be used in assays to detect specific genes, gene segments and other nucleic acids. These assays will have clinical potential in a wide variety of areas such as medicine, environmental studies, biological research etc. The present technology relies on EPR probes attached to nucleic acids and makes use of the resonance properties of the EPR labels that are affected by complex in part still poorly understood factors in the immediate environment of the probe.

The present invention also provides for a kit for direct EPR detection of specific PCR amplified target nucleic acid sequences.

The outlined nitroxide label approach can be used in assays to detect specific genes, gene segments and other nucleic acids. These assays will have clinical potential in a wide variety of areas such as medicine, environmental studies, biological research etc. The potential market value can be envisioned in millions of dollars!

DETAILED DESCRIPTION OF THE INVENTION

Figure 1:
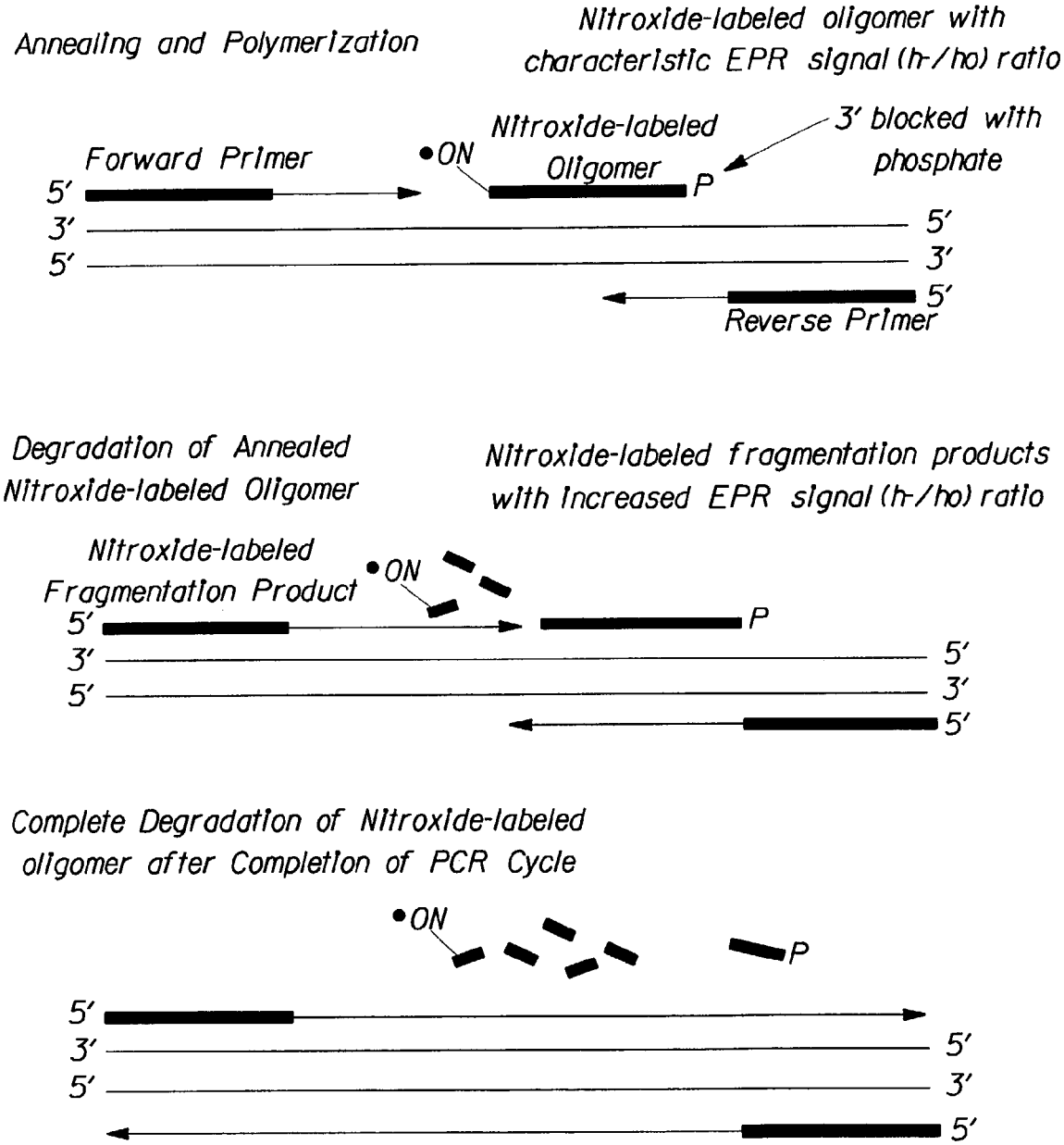
FIG. 1: PCR reaction scheme with for instance 100 pmol nitroxide-labeled oligomer that is only degraded if the amplified target (amplicon) can hybridize to the nitroxide-labeled oligomer. The fact that the EPR detection relies on PCR means that in principle only a few target molecules are needed for the assay to work.

To aid in understanding the invention, several terms are defined below.

The terms "nucleic acid" and "oligonucleotide" refer to primers, probes, and oligomer fragments to be detected, and shall be generic to polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine base. There is no intended distinction in length between the terms "nucleic acid" and "oligonucleotide", and these terms will be used interchangeably. These terms refer only to the primary structure of the molecule. Thus, these terms include double-and single-stranded DNA, as well as double- and single-stranded RNA.

The exact size of an oligonucleotide depends on many factors and the ultimate function or use of the oligonucleotide. Oligonucleotides can be prepared by any suitable method, including, for example, cloning and restriction of appropriate sequences and direct chemical synthesis by a method such as the phosphotriester method of Narang et al., 1979, Meth. Enzymol. 68:90–99; the phosphodiester method of Brown et al., 1979, Meth. Enzymol. 68:109–151; the diethylphosphoramidite method of Beaucage et al., 1981, Tetrahedron Lett. 22:1859–1862; and the solid support method of U.S. Pat. No. 4,458,066, each incorporated herein by reference. A review of synthesis methods is provided in Goodchild, 1990, Bioconjugate Chemistry 1(3):165–187, incorporated herein by reference.

The term "target region" refers to a region of a nucleic acid that is to be analyzed.

The term "hybridization" refers the formation of a duplex structure by two single stranded nucleic acids due to complementary base pairing. Hybridization can occur between complementary nucleic acid strands or between nucleic acid strands that contain minor regions of mismatch. Conditions under which only complementary nucleic acid strands will hybridize are referred to as "stringent hybridization conditions." Two single-stranded nucleic acids that are complementary except for minor regions of mismatch are referred to as "substantially complementary". Stable duplexes of substantially complementary sequences can be achieved under less stringent hybridization conditions. Those skilled in the art of nucleic acid technology can determine duplex stability empirically considering a number of variables including, for example, the length and base pair concentration of the oligonucleotides, ionic strength, temperature, and incidence of mismatched base pairs.

The term "probe" refers to an oligonucleotide that forms a duplex structure with a sequence of a target nucleic acid due to complementary base pairing. The probe will contain a "hybridizing region", which is a region of the oligonucleotide corresponding to a region of the target sequence. "Corresponding" means identical to or complementary to the designated nucleic acid. An oligonucleotide probe can either consist entirely of the hybridizing region or can contain additional features that allow for the detection or immobilization of the probe but do not alter the hybridization characteristics of the hybridizing region. As used herein, the term "probe" also refers to a set of oligonucleotides, wherein the oligonucleotides of the set provide sufficient sequence variants of the hybridization region to enable hybridization with each member of a given set of target sequence variants.

The term "EPR probe", as used herein, encompasses the sequence-specific oligonucleotides used in the procedures of the present invention that contain labels detectable by electron spin resonance ("ESR"), also known as electron paramagnetic resonance ("EPR"), spectroscopy. Preferably, the EPR probes are labeled with a nitroxide. Nitroxide labeled nucleotides and nitroxide labeled hybridization probes are known in the art as described in U.S. Pat. No. 5,004,809, incorporated herein by reference. Besides using the already known nitroxide labeled hybridization probes, it is foreseen many other nitroxide labeled oligonucleotides may be prepared using known methods. The term "h" is the signal height or peak-to-peak height as measured by ESR. "$h_1/h_0$" is the ration of the signal height after amplification or degradation compared to original signal height.

"Sample", as used herein, refers to any substance containing or presumed to contain the target nucleic acid sequence and includes a sample of tissue or fluid isolated from an individual, including but not limited to, skin, plasma, serum, spinal fluid, lymph fluid, synovial fluid, urine, tears, blood cells, organs, tumors, in vitro cell cultures constituents, for example.

The term "primer" refers to an oligonucleotide, whether natural or synthetic, capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The appropriate length of a primer depends on the intended use of the primer but typically ranges from 15 to 35 nucleotides. Short primer molecules generally require cooler temperatures to form sufficiently stable hybrid complexes with the template. A primer need not reflect the exact sequence of the template but must be sufficiently complementary to hybridize with a template. Primers can incorporate additional features which allow for the detection or immobilization of the primer but do not alter the basic property of the primer, that of acting as a point of initiation of DNA synthesis. The oligonucleotide primers and probes can be synthesized in a variety of known ways, such as on any Perkin-Elmer Applied Biosystem DNA synthesizer.

As used herein, the term "primer" also refers to a set of oligonucleotides, wherein the oligonucleotides of the set provide sufficient sequence variants of the hybridization region to enable hybridization with each member of a given set of target sequence variants, so as to act as a point of initiation of DNA synthesis. Additionally, a primer may consist of one or more oligonucleotides which contain mismatches with some or all members of a given set of target sequence variants, but contains sufficient regions of complementarity with each target sequence variant so as to enable hybridization with all target sequence variants under suitable conditions. The term "consensus primers" is used herein to refer to single oligonucleotides complementary to a consensus target sequence, to primers consisting of multiple oligonucleotides, and to combinations thereof.

The term "thermostable polymerase enzyme" refers to an enzyme that is relatively stable to heat and catalyzes the polymerization of nucleoside triphosphates to form primer extension products that are complementary to one of the nucleic acid strands of the target sequence. The enzyme initiates synthesis at the 3' end of the primer and proceeds in the direction toward the 5' end of the template until synthesis terminates. Any suitable nucleic acid polymerase having 5' to 3' exonuclease activity and devoid of 3' to 5' exonuclease activity can be employed in the procedure of this invention. The nucleic acid polymerase hydrolyses the oligonucleotide analytical probe only when the probe is hybridized to the target nucleic acid sequence. Preferably employed is a thermostable nucleic acid DNA polymerase, such as those disclosed in U.S. Pat. No. 4,889,818, incorporated herein by reference. Especially preferred for use is the Thermus aquaticus DNA polymerase available from Perkin-Elmer as AMPLITAQ® DNA polymerase.

Hybridization probes of the invention can be made from DNA, RNA, or some combination of the two. The probes may include modified nucleotides. Modified internucleotide linkages are useful in probes comprising deoxyribonucleotides and ribonucleotides to alter, for example, the hybridization strength. The links between nucleotides in the probes may include bonds other than phosphodiester bonds, but they have all to be sensitive toward nuclease digestion.

The present invention relates generally to the preparation and use of nucleic acid primers in the detection of sequence variations, mutations and the like, in DNA samples. Primers are DNA molecules that are employed to "prime" the synthesis or copying of a "template" DNA strand by a DNA polymerase enzyme into a complementary strand. The newly generated complementary strand will elongate from the primer into a new strand that remains bound or hybridized to the template strand unless denatured.

In nature, DNA polymerases are required in order to catalyze DNA synthesis prior to cell division, providing an "extra", exact copy or replica of a cell's genomic DNA molecule to the daughter cells. The cell's entire DNA complement is copied prior to cell division, through copying of each strand into a complementary strand. Each DNA strand has a defined polarity, a "3' direction" and a "5' direction", governed by the head-to-tail arrangement of the pentose-phosphate backbone. The ribose molecule portion of the pentose-phosphate backbone has a 5' carbon and a 3' carbon linked to adjacent ribose molecules through a phosphate molecule. Furthermore, complementary DNA strands run in an "anti-parallel" direction with respect to each other, with one strand running in an opposite direction of its complement. Thus, a 3' direction on one strand corresponds to a 5' direction on the complement.

In order to achieve the enzymatic copying of a DNA strand, whether in a cell (in vivo) or in a test tube (in vitro), the DNA polymerase enzyme must have a starting point from which to begin its synthesis. This starting point is the 3' terminus of the "primer" or "priming strand". The primer is annealed to the template strand at a position at which DNA synthesis begins. During DNA replication, the DNA polymerase enzyme begins copying of the template strand at the 3' end of the priming strand and forms a covalent phosphate linkage with the 5' carbon of the growing chain. Due to the fact that DNA replication has a 3' to 5' polarity of elongation, synthesis proceeds in a 3' direction with respect to the strand that is being copied (the template).

Amplification of a selected, or target, nucleic acid sequence may be carried out by many suitable means. See generally D. Kwoh and T. Kwoh, Am. Biotechnol. Lab. 8, 14–25 (1990). Examples of suitable amplification techniques include, but are not limited to, polymerase chain reaction, ligase chain reaction, strand displacement amplification (see generally G. Walker et al., Proc. Natl. Acad. Sci. U.S.A. 89, 392–396 (1992); G. Walker et al., Nucleic Acids Res. 20, 1691–1696 (1992)), transcription-based amplification (see D. Kwoh et al., Proc. Natl. Acad Sci. U.S.A. 86, 1173–1177 (1989)), self-sustained sequence replication (or "3SR") (see J. Guatelli et al., Proc. Natl. Acad. Sci. U.S.A. 87, 1874–1878 (1990)), the Q beta replicase system (see P. Lizardi et al., BioTechnology 6, 1197–1202 (1988)), nucleic acid sequence-based amplification (or "NASBA") (see R. Lewis, Genetic Engineering News 12 (9), 1 (1992)), the repair chain reaction (or "RCR") (see R. Lewis, supra), modified ligase chain reaction (or "Gap-LCR") (see K. Abravaya et al., Nucleic Acids Res., 23, 675–682 (1995)), and boomerang DNA amplification (or "BDA") (see R. Lewis, supra). Polymerase chain reaction is currently preferred.

Polymerase chain reaction (PCR) is a known and well-established technique. See, e.g., U.S. Pat. Nos. 4,683,195; 4,683,202; 4,800,159; and 4,965,188. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized which is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product, the probe carrying a detectable label, and then detecting the label in accordance with known techniques, or by direct visualization on a gel.

The use of the PCR or site-specific DNA amplification technique, in combination with synthetic oligodeoxynucleotides is often employed to detect point mutations. A dot blot screening procedure for mutated ras oncogenes using synthetic oligonucleotides involves the specific in vitro amplification of genetic regions suspected of containing a particular, known mutation in a specific configuration, followed by hybridization of the amplified DNA under tightly controlled parameters with one or more oligonucleotides which carry complementary mutations. By determining which of the oligonucleotides bind tightly under the specified hybridization conditions, one can attempt to ascertain which, if any, of the mutations are present in the segment of the DNA that is amplified. This technique requires several steps, including both an amplification step followed by a separate hybridization step. Furthermore, the technique relies upon very tightly controlled hybridization conditions, thus rendering it generally inapplicable to everyday clinical application.

Ligase chain reaction ("LCR") is another amplification method carried out in accordance with known techniques. See, e.g., R. Weiss, Science 254, 1292 (1991). In general, the reaction is carried out with two pairs of oligonucleotide probes: one pair binds to one strand of the sequence to be detected; the other pair binds to the other strand of the sequence to be detected. Each pair together completely encompasses the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

In LCR, targets that differ by a single base pair are discriminated, since a mismatch at the ligation joint severely reduces the efficiency of ligation. Generation of target-independent ligation products due to blunt-end ligation poses limitations on the sensitivity of LCR. Typically, the sensitivity of LCR or any diagnostic assay is not a critical factor for detection of mutations in human genetic diseases, where 50 or 100% of DNA contains the mutation. In contrast, for detection of somatic mutations within oncogenes, tumor suppressor genes or drug resistance mutations, where a small number of mutated molecules need to be detected in the presence of excess wild-type DNA, sensitivity becomes a critical factor.

Several approaches have been taken to increase the sensitivity of LCR. One approach has been to use another amplification technology, such as PCR, followed by limited amplification with LCR. Other alternatives are PCR followed with the ligation detection reaction ("LDR"), where only two adjacent probes are used, resulting in linear amplification, or PCR followed with the oligonucleotide ligation analysis ("OLA"), where ligation of two adjacent probes is used as 3 single detection step. However these combined approaches necessitate the opening of tubes after PCR, generating a source of contamination and also introducing complexity to automation.

A modification of LCR, "Gap-LCR," has been introduced to circumvent these difficulties and improve the sensitivity of LCR. In Gap-LCR, complementary probe pairs containing 3' extensions are used. Using this technique, after hybridization to target DNA, a gap of one to several bases exists between adjacent probes. A thermostable DNA polymerase, devoid of 3'—>5' exonuclease activity, and the appropriate nucleotide(s) are used to fill the gap and the resultant probes are joined by DNA ligase. The use of probe duplexes with non-complementary 3' extensions prevents the generation of target-independent ligation products. Amplification products are detected by a sandwich immunoassay performed with an automated analyzer.

Another approach that has found some usefulness in connection with certain genetic disorders involves the use of restriction enzyme analysis of DNA to identify changes in restriction fragmentation pattern of the suspected or selected DNA in comparison with a standard or reference DNA. In one approach employing restriction enzyme analysis, the selected and reference DNA's are simply compared, side-by-side, using various restriction enzyme digestions. An alteration in the digestion pattern of the selected DNA versus the reference DNA is indicative of a mutation, such as an insertion or deletion.

In one embodiment, the present invention provides a method for detecting the presence or absence of a target nucleic acid sequence in a sample, said process comprising:
  a) providing in a PCR reaction mixture a sample suspected to contain a target nucleic acid sequence, oligonucleotide PCR primers that hybridize to the target nucleic acid sequence for PCR amplification of said target sequence, each of four deoxynucleoside triphosphates, nucleic acid polymerase having 5' to 3' exonuclease activity and devoid of 3' to 5' exonuclease activity, and an EPR-labeled oligonucleotide analytical probe (EPR probe)
  b) amplifying target nucleic acid sequence in the sample under suitable PCR reaction mixture temperature conditions by a repetitive series of PCR thermal cycling steps comprising:
    1) denaturing the target nucleic acid sequence into opposite strands;
    2) hybridizing the EPR probe within the target nucleic acid sequence of the denatured strands and hybridizing the oligonucleotide PCR primers to the denatured strands, and
    3) extending the hybridized primers with the four deoxynucleoside triphosphates and the nucleic acid polymerase, and producing preferentially 5' EPR labeled nucleotide fragments during this extension phase by the 5' to 3' exonuclease activity of the nucleic acid polymerase on EPR probe annealed to the denatured strands;
  c) following amplification of the target nucleic acid sequence by one or more series of thermal cycling steps, detecting or measuring the magnetic resonance as a measure of the presence of the target nucleic acid sequence.

In the temperature range at which the PCR thermal cycling steps occur the oligonucleotide analytical EPR probe anneals to a denatured strand of the target nucleic acid sequence and during the PCR extension phase the invention utilizes the 5' to 3' exonuclease activity of the nucleic acid polymerase to produce preferentially 5' EPR labeled nucleotide fragments by hydrolysis of the nucleotides of oligonucleotide analytical probe annealed to the denatured strand.

Figures 2A, 2B:
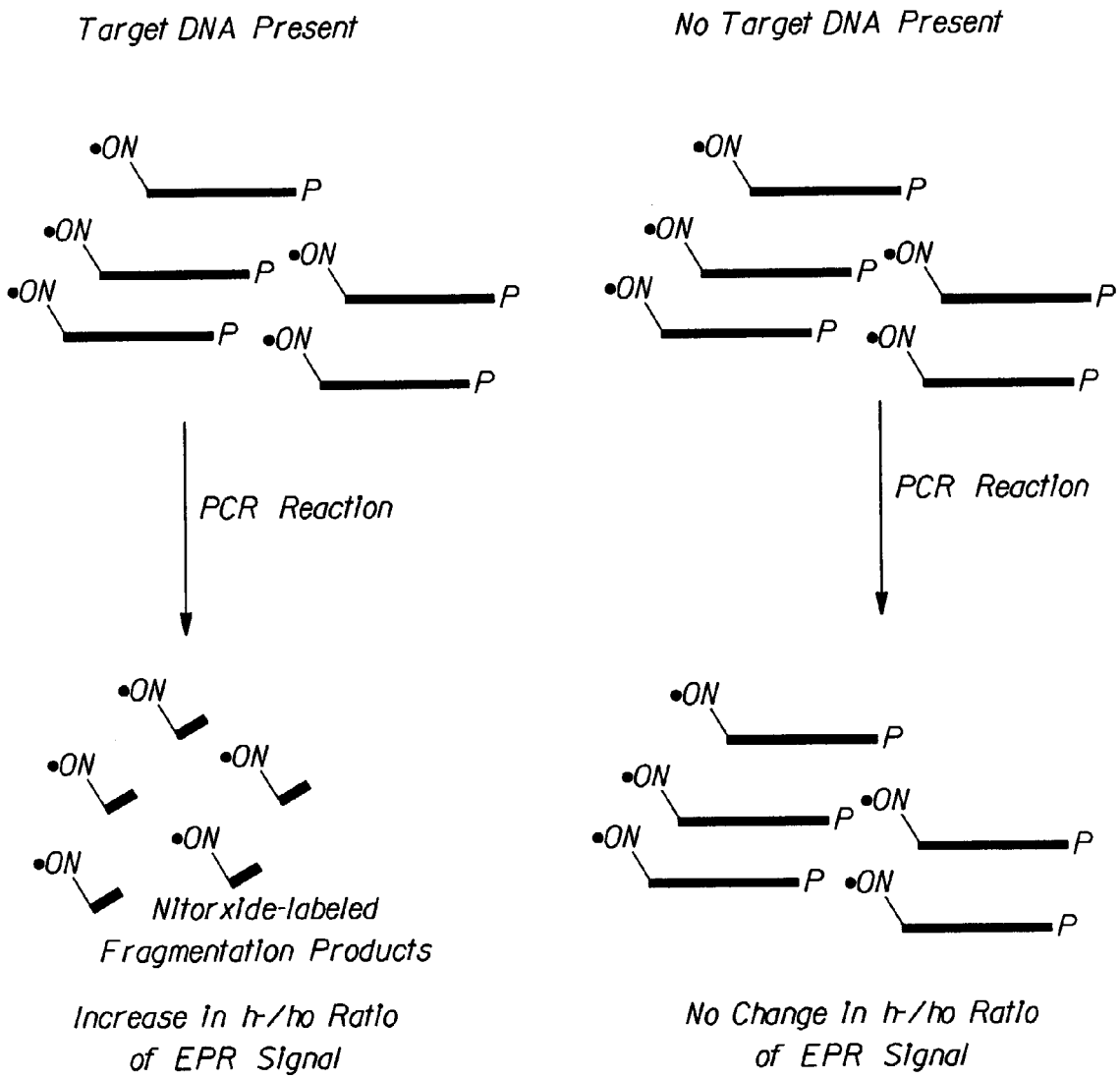
FIG. 2: Detection strategy with EPR. Left: The $h_{-1}h_0$ ratio of the EPR signal of the nitroxide increases if the amplified target sequence hybridizes to the nitroxide-labeled oligomers. The increase in the $h_{-1}h_0$ ratio is due to the formation of nitroxide-labeled fragmentation products. Right: No change in the EPR signal of the nitroxide due to the absence of complementary target DNA thereby preventing the degradation of the nitroxide-labeled oligomer. The EPR line shape change is due to the increased tumbling rate of the nitroxide moiety upon its release from the oligonucleotide.
Figure 3A:
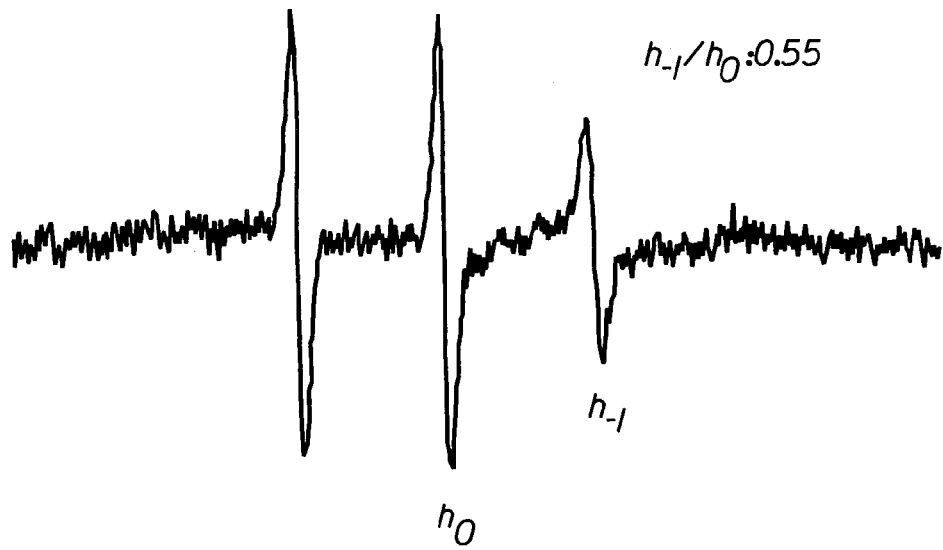
FIG. 3: Characteristic EPR signals of spin (nitroxide)—labeled hybridization probes: A) 19-mer with nitroxide away from 5'-end, B) 25-mer with nitroxide at 5'-end; note the position of $h_0$ and $h_1$ and the value of the $h_{-1}h_0$ ratio that is in each case smaller than 0.7.
Figure 3B:
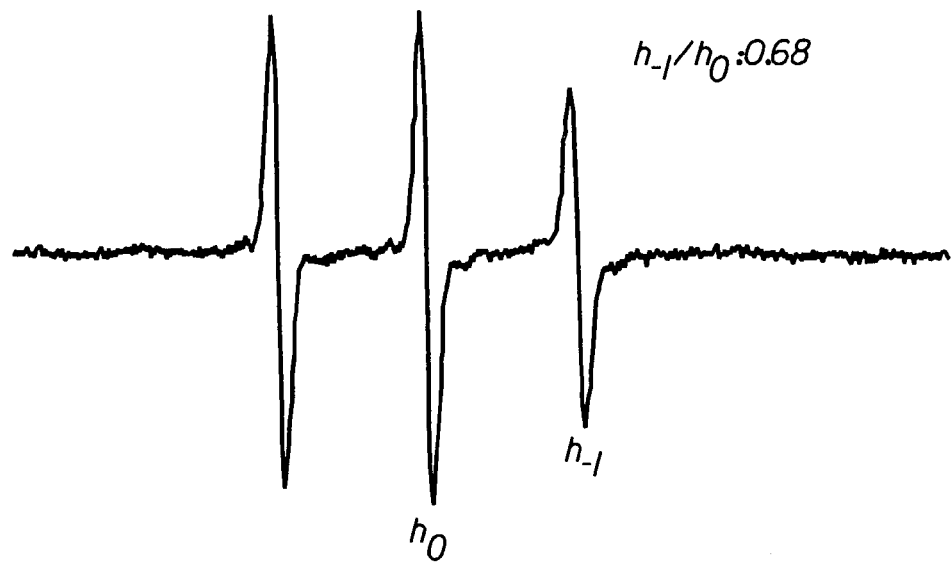

Characteristic EPR signals of two nitroxide-labeled oligomers are shown in FIG. 3; A) 0.17 nmol nitroxide-labeled 19-mer with the label away from the 5'-end and B) 0.32 nmol nitroxide-labeled 25-mer with the label at the 5'-end, in both cases their characteristic $h_0$ and $h_{-1}$ peaks are indicated. For the EPR assay the signal height of these two peaks has to be determined. The formation of nitroxide-labeled fragments from the oligomers due to nuclease digestion in the presence of the nucleic acid target (see FIG. 2) results in an increase of the original $h_{-1}/h_0$ ratio. This increase in ratio is attributed to a faster motion of the nitroxide-labeled fragments than the nitroxide-labeled oligomers.

Figure 4A:
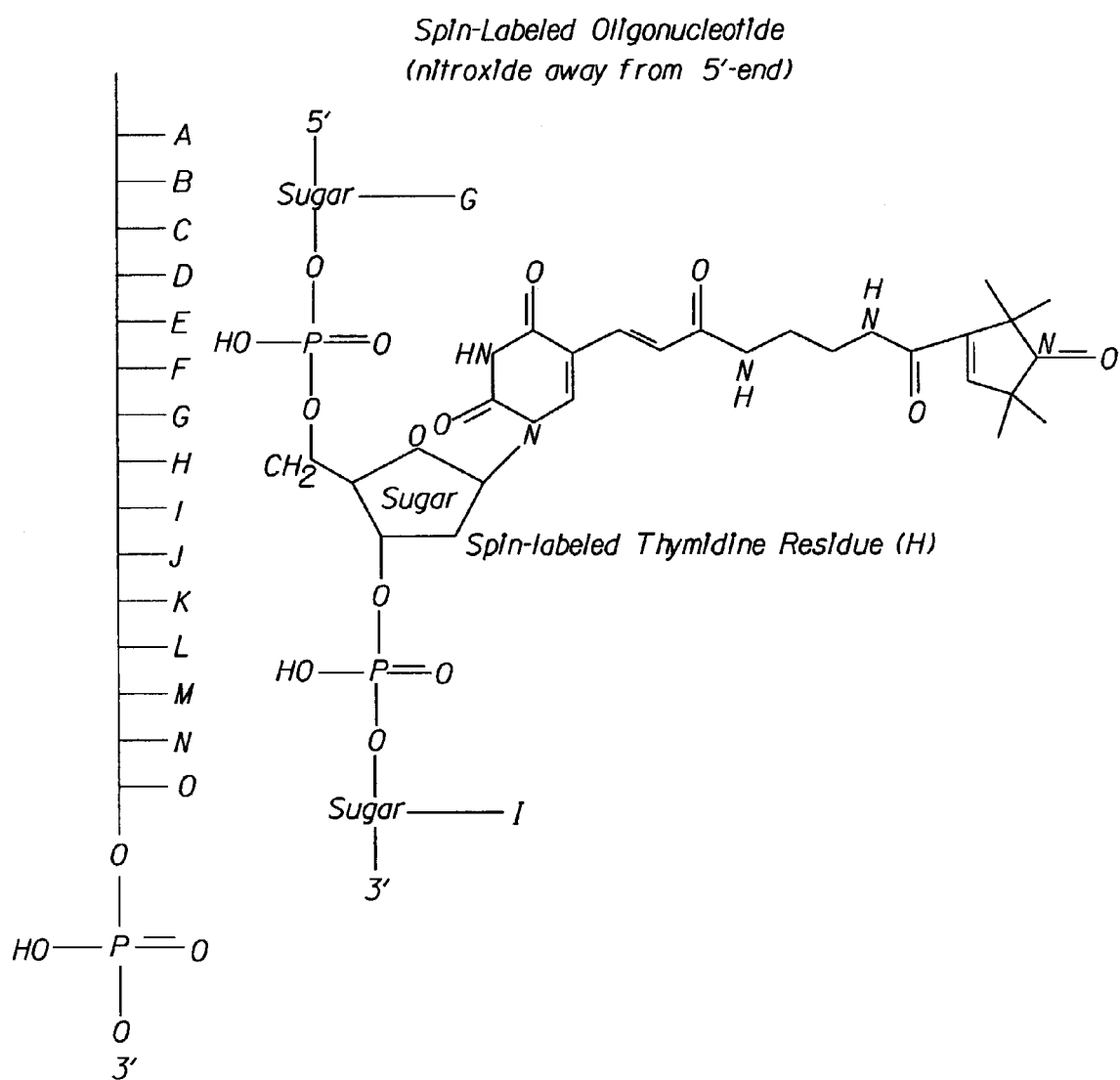
FIG. 4: Chemical structure of two typical nitroxide-labeled hybridization probes. A) nitroxide is positioned away from the 5'-end; B) nitroxide is attached at the 5'-end.
Figure 4B:
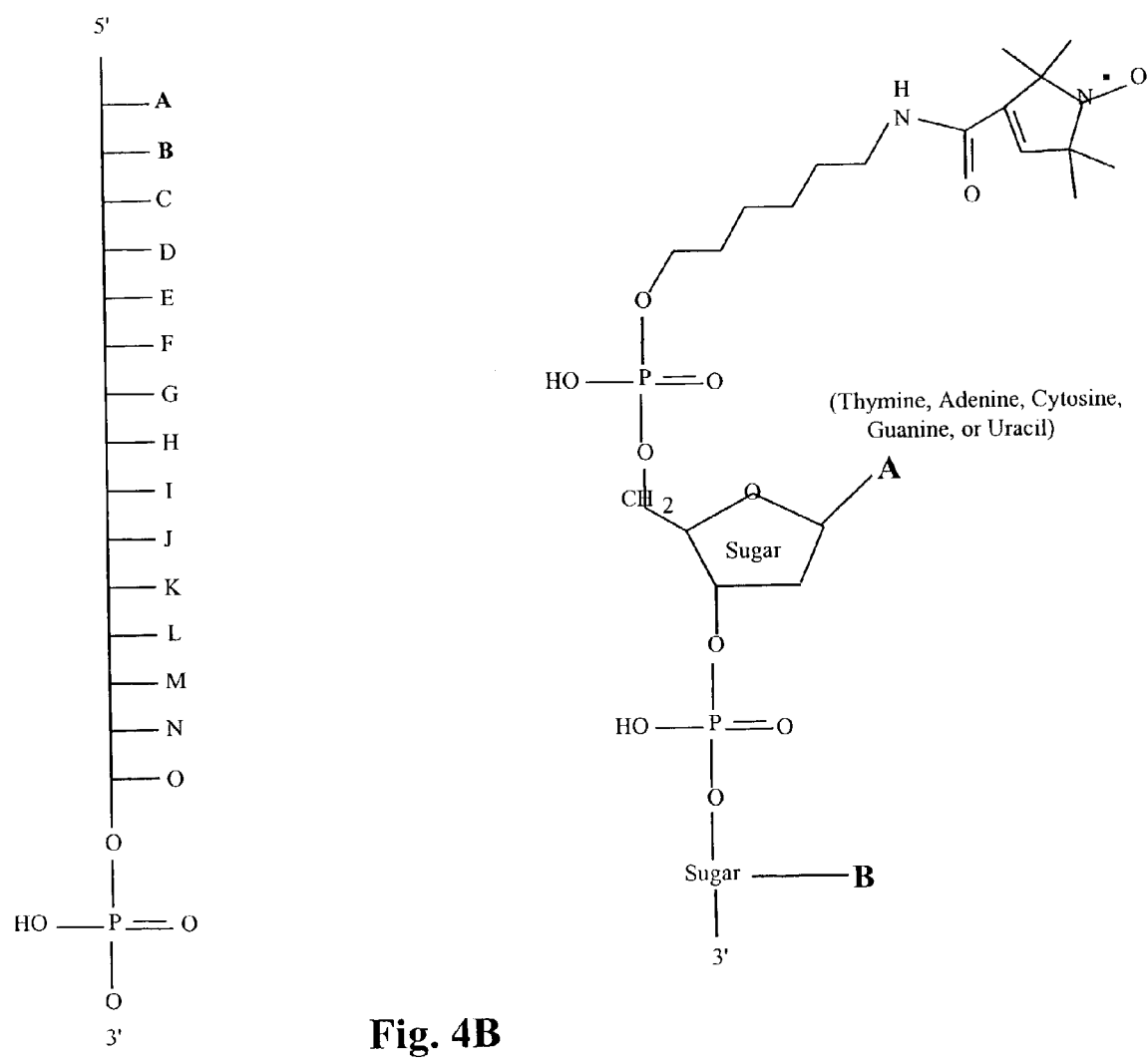

FIG. 4 shows the chemical structure of two typical nitroxide (spin)-labeled oligomers. In one case the nitroxide is away from the 5'-end and in the other case it is at the 5'-end. Note the small size of the nitroxide label that has a molecular weight that is at least a factor of 4 smaller than the one of commonly used fluorescent labels.

In contrast to approaches based on fluorescence spectroscopy developed by others the proposed magnetic resonance detection (EPR) with nitroxide labeled oligomers offers the advantage of no interference by turbidity of the solution, no interference by the hydrophobic properties of the fluorochromes, no tedious and expensive labeled oligomer synthesis, but most importantly, no interference by potential fluorescent background signals. While the fluorescent based technology relies on some complex mechanism responsible for the increase of fluorescence in the presence of two labels (one with fluorescent and one with quenching properties) in the PCR mixture, the nitroxide-labeled oligomer based assay relies on a theoretically more readily understood EPR line-shape change (h-/ho ratio change) due to one label only, namely the nitroxide label, whereas fluorescent based assays usually require two labels.

Nitroxide labeled nucleotides and nitroxide labeled hybridization probes are known in the art as described in U.S. Pat. No. 5,004,809, incorporated herein by reference. Besides using the already known nitroxide labeled hybridization probes, it is foreseen many other nitroxide labeled oligonucleotides may be prepared using known methods.

The nitroxide label methods of the present invention can be used in assays to detect specific genes, gene segments and other nucleic acids. These assays will have clinical potential in a wide variety of areas such as medicine, environmental studies, biological research etc. The present technology relies on EPR probes attached to nucleic acids and makes use of the resonance properties of the EPR labels that are affected by complex in part still poorly understood factors in the immediate environment of the probe.

Generally, the EPR probes can be identified by EPR spectroscopy over a relatively narrow wave band with an EPR instrument by time averaging two or more distinct peaks with relatively small quantities of EPR probes. Alternately, the EPR probes can be identified by EPR spectroscopy by time averaging three or more distinct peaks.

The degradation of the nitroxide-labeled oligomers into nitroxide-labeled cleavage products results in a characteristic increase of the h-/ho or $h_1/h_0$ ratio of the EPR signal. With the present invention, hybridization gives rise to an increase of the signal intensity, which together with the amplification process allows for single genome detection by analyzing two distinct peaks. Preferably, the peaks are analyzed using a dedicated EPR instrument. The primary feature is the unexpected reaction of the behavior of the probes when brought together in close proximity.

In the present invention, the degradation of the nitroxide-labeled oligomers into nitroxide-labeled cleavage products results in a characteristic increase of the $h_1/h_0$ ratio of the EPR signal; in the absence of a complementary target sequence the EPR signal of nitroxide-labeled oligomer remains unchanged. For the EPR assay of the present invention, the signal height of characteristic $h_0$ and $h_{-1}$ peaks have to be determined. A release of the nitroxide from the oligomer results in a characteristic increase of the $h_1/h_0$ ratio due to the formation of nitroxide-labeled cleavage products. The $h_1/h_0$ ratio of the EPR signal of the nitroxide increases only if the amplified target sequence hybridizes to the nitroxide-labeled oligomers.

While the fluorescent based technology of previously known methods relies on some complex mechanism responsible for the increase of fluorescence in the presence of two labels (one with fluorescent and one with quenching properties) in the PCR mixture, the nitroxide-labeled oligomer based assay of the present invention relies on an easily understood EPR lineshape change ($h_1/h_0$ ratio change) of one label only, namely the nitroxide label.

The present invention also provides for a kit for direct EPR detection of specific PCR amplified target nucleic acid sequences. The PCR reaction is carried out in the presence of nitroxide-labeled oligomers that are degraded only if hybridized to a complementary target sequence (see FIG. 1). The degradation of the nitroxide-labeled oligomers into nitroxide-labeled cleavage products results in a characteristic increase of the h-/ho ratio of the EPR signal; in the absence of a complementary target sequence the EPR signal of nitroxide-labeled oligomer remains unchanged (see FIG. 2).

The outlined nitroxide label approach can be used in assays to detect specific genes, gene segments and other nucleic acids. These assays will have clinical potential in a wide variety of areas such as medicine, environmental studies, biological research, etc.

With the foregoing description of the invention, those skilled in the art will appreciate that modifications may be made to the invention without departing from the spirit thereof. Therefore, it is not intended that the scope of the invention be limited to the specific embodiments illustrated and described.

The invention claimed is:

1. A method for detecting the presence or absence of a target nucleic acid sequence in a sample, said method comprising:
   a) providing in a PCR reaction mixture a sample suspected to contain a target nucleic acid sequence, oligonucleotide PCR primers that hybridize to the target nucleic acid sequence for PCR amplification of said target sequence, each of four deoxynucleoside triphosphates, nucleic acid polymerase having 5' to 3' exonuclease activity and devoid of 3' to 5' exonuclease activity, and an EPR-labeled oligonucleotide analytical probe (EPR probe);
   b) amplifying target nucleic acid sequence in the sample under suitable PCR reaction mixture temperature conditions by a repetitive series of PCR thermal cycling steps comprising:
      1) denaturing the target nucleic acid sequence into opposite strands;
      2) hybridizing the EPR probe within the target nucleic acid sequence of the denatured strands and hybridizing the oligonucleotide PCR primers to the denatured strands, and
      3) extending the hybridized primers with the four deoxynucleoside triphosphates and the nucleic acid polymerase, and producing 5' EPR labeled nucleotide fragments during this extension phase by the 5' to 3' exonuclease activity of the nucleic acid polymerase on the EPR probes annealed to the denatured strands; and
   c) measuring the EPR resonance signals produced by degradation of EPR-labeled probes by magnetic resonance as a measure of the presence of the target nucleic acid sequence following amplification of the target nucleic acid sequence by one or more series of thermal cycling steps;
   wherein the 5' EPR labeled nucleotide fragments produced are measured by measuring EPR signal $h_0$ and $h_{-1}$ peaks and detecting a change in the original $h_{-1}/h_0$ ratio.

2. The method of claim 1 wherein 5' EPR labeled nucleotide fragments formed are detected or measured by magnetic resonance detection (EPR) and provide single genome detection.

3. The method of claim 2, wherein the 5' EPR labeled nucleotide fragments formation results in a characteristic increase of the $h_{-1}/h_0$ ratio of the magnetic resonance detection (EPR) signal.

4. The method of claim 3 wherein the probe sequence is selected from the group consisting of DNA, RNA, and mixtures of DNA and RNA.

5. The method of claim 4 wherein the nucleic acid polymerase is Thermus aquaticus DNA polymerase or any other thermo stable polymerase.

6. The method of claim 5 wherein the oligonucleotide analytical probe is labeled with a nitroxide.

7. The method of claim 6 wherein the oligonucleotide analytical probe sequence is from about 10 to about 140 nucleotides complementary to said nucleic acid target sequence, having a 5' terminus and a 3' terminus.

8. The method of claim 1, wherein a detected increase of the original $h_{-1}/h_0$ ratio indicates the presence of the target nucleic acid sequence in the segment of the DNA that is amplified.

9. The method of claim 3, wherein the release of the nitroxide from the oligomer results in the $h_{-1}/h_0$ ratio having a value greater than about 0.7.

* * * * *